US00PP10083P

United States Patent [19]

Olesen et al.

[11] Patent Number: Plant 10,083

[45] Date of Patent: Oct. 28, 1997

[54] MINIATURE ROSE PLANT NAMED 'POULFECT'

[75] Inventors: Mogens N. Olesen; Pernille Olesen, both of Fredensborg, Denmark

[73] Assignee: Bear Creek Gardens, Inc., Medford, Oreg.

[21] Appl. No.: 606,894

[22] Filed: Feb. 21, 1996

[51] Int. Cl.[6] ..... A01H 5/00

[52] U.S. Cl. ..... Plt./9

[58] Field of Search ..... Plt./7.1, 9

*Primary Examiner*—Howard J. Locker

*Attorney, Agent, or Firm*—Klarquist Sparkman Campbell Leigh & Whinston, LLP

[57] ABSTRACT

A miniature rose plant having well formed, nonfading salmon colored flowers; compact even growth when grown in a pot; long shelf life, and being readily propagated by softwood cuttings.

1 Drawing Sheet

The present invention relates to a new and distinct variety of rose plant of the miniature class which was originated by us by crossing an unnamed seedling, unpatented, with the variety RUIforto, U.S. Plant Pat. No. 6244.

The primary objective of this breeding was to produce a new rose variety having the vigorous upright growth, well formed salmon colored flowers and healthy dark green foliage of the unnamed female seedling combined with the miniature habit and smaller flower size of the male parent RUIforto. The objective was substantially achieved, along with other desirable improvements, as evidenced by the following unique combination of characteristics that are outstanding in the new variety and that distinguish it from its parents, as well as from all other varieties of which we are aware:

1. Attractive, nonfading, salmon colored flowers;
2. Long shelf life in bloom;
3. Compact, even growth making it ideal for pot culture; and
4. Ease of propagation from softwood cuttings.

Asexual reproduction of this new variety by softwood cuttings, as performed at Wasco and Somis, Calif., and Fredensborg, Denmark, shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—Unnamed seedling.

*Pollen parent.*—RUIforto.

Classification:

*Botanical.*—*Rosa hybrida.*

*Commercial.*—Miniature.

FLOWER

Observations made from specimens grown in a greenhouse environment at Somis, Calif., and Fredensborg, Denmark.

Blooming habit: Continuous.

Bud:

*Size.*—⅝ inch long when the petals start to unfurl.

*Form.*—The bud form is short, pointed ovoid.

*Color.*—When sepals first divide, bud color is Red Group 38A. When half blown, the upper sides of the petals are Red Group 38A; and the lower sides of the petals are Red Group 49A.

*Sepals.*—Color: Green Group 138A. Surface texture: Covered in fine hairs. There are three lightly appendaged sepals. There are two unappendaged sepals with hairy edges that also have a few glands.

*Receptacle.*—Color: Green Group 143A. Shape: Funnel. Size: Small (¼" ×3/16"). Surface: Smooth.

*Peduncle.*—Length: Short (1½" to 1¾"). Surface: Smooth. Color: Medium green. Strength: Stiff and erect.

Bloom:

*Size.*—Small. Average open size is 1½ inches to 1¾ inches.

*Borne.*—Singly, several together, in pyramidal clusters of 3–5 flowers.

*Stems.*—Short (6"–8") and strong.

*Form.*—When first open: High center. Permanence: Flattens and outer petals curl back.

*Petalage.*—Number of petals under normal conditions: 30–35.

*Color.*—The upper side of the petals is Red Group 38A. The reverse side of the petals is Red Group 49A. The base of each petal has a small (⅛"×⅛") Yellow Group 3D half moon at the point of attachment. The major color on the upper side is Red Group 38A.

*Variegations.*—Occasional whitish streak on the reverse side of the guard petals.

*Discoloration.*—There is no change in the color of the petals until they drop on day 7 or 8.

*Fragrance.*—None.

*Shelf life.*—Under low light urban conditions, Plant will remain in bloom for 15 or more days.

Petals:

*Texture.*—Thick and leathery.

*Shape.*—Round to slightly deltoid.

*Form.*—Tips slightly recurved.

*Arrangement.*—Imbricated, with few petaloids in the center.

*Persistence.*—Drop off cleanly.

*Lastingness.*—On the plant: Long, 7–8 days. As a cut flower: Not tested.

Reproductive Parts:

*Anthers.*—Size: Medium. Quantity: Many. Color: Yellow. Arrangement: Regular around styles.

*Filaments.*—Color: White.

*Pollen.*—Color: Lemon yellow.

*Styles.*—Color: Reddish.

*Stigmas.*—Color: White.

Form: Bush.

Growth: Vigorous, dwarf, upright, branching, compact. Plant in a 5 inch container will be 10–12 inches tall.

Foliage: Number of leaflets on normal mid-stem leaves: 5 or 7.

*Size.*—Small (3–3¾"×2–2¼").

*Quantity.*—Abundant.

*Color.*—New foliage: Very little anthocyanin. Upper: Green Group 137A. Lower: Green Group 138B with some reddish pigment on the margins of the youngest leaves. Old foliage: Upper: Green Group 139A. Lower: Green Group 138B.

Leaflets:

*Shaped.*—Pointed oval.

*Texture.*—Upper side: Glossy and smooth.

*Edge.*—Serrated.

*Serration.*—Single and small.

*Petiole rachis.*—Color: Green.

*Petiole underside.*—Smooth with occasional prickles.

*Stipules.*—Short (¼"), serrated and bearded.

*Disease resistance.*—Resistant to mildew under normal growing conditions at Somis, Calif.

Wood:

*New wood.*—Color: Light green. Bark: Smooth.

*Old wood.*—Color: Green. Bark: Smooth.

Prickles:

*Quantity.*—On main canes from base: Ordinary. On laterals from main canes: Ordinary.

*Form.*—Short (3/16") and straight.

*Color when young.*—Red.

Small prickles:

*Quantity.*—On main stalks: None. On laterals: None.

*Related varieties.*—POULavon, application Ser. No. 08/605821, filed Feb. 21, 1996, is a mutation of POULfect, differing only in flower color.

We claim:

1. A new and distinct variety of rose plant of the miniature class, substantially as herein shown and described, characterized particularly as to novelty by the combination of its attractive, nonfading salmon colored flowers; compact even growth under pot culture; long shelf life; and ease of propagation from softwood cuttings.

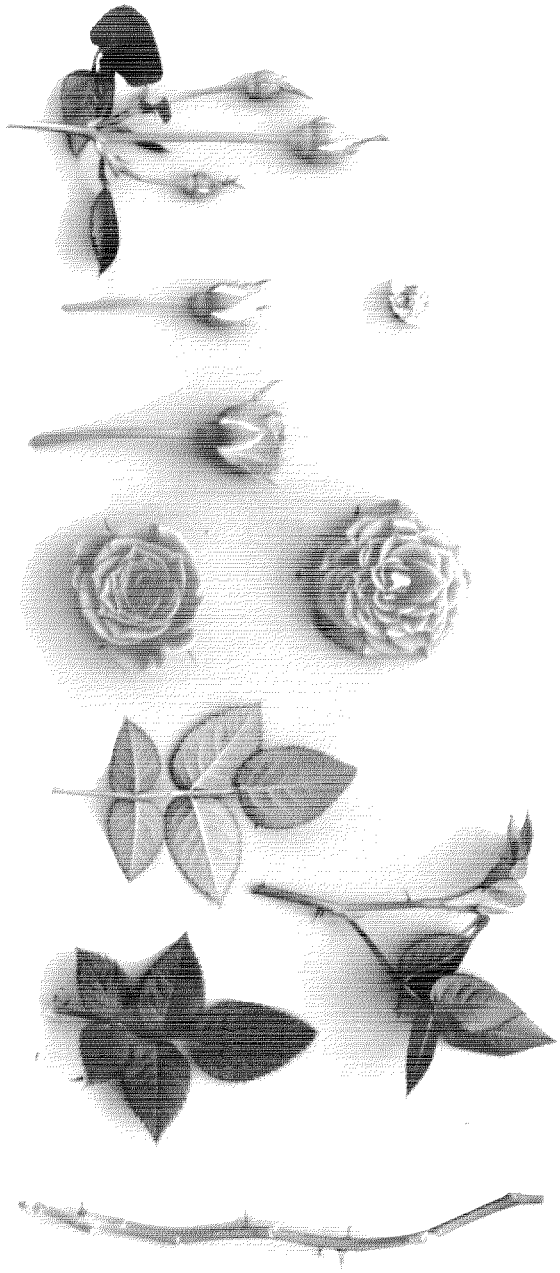

* * * * *